(12) United States Patent
Hancock et al.

(10) Patent No.: US 10,568,689 B2
(45) Date of Patent: Feb. 25, 2020

(54) SURGICAL SNARE WITH ABILITY TO DELIVER ELECTROMAGNETIC ENERGY AND/OR THERMAL PLASMA INTO BIOLOGICAL TISSUE

(71) Applicant: Creo Medical Limited, Chepstow Monmouthshire (GB)

(72) Inventors: Christopher Paul Hancock, Bath (GB); Malcolm White, Chepstow (GB)

(73) Assignee: CREO MEDICAL LIMITED, Monmouthshire (GB)

( * ) Notice: Subject to any disclaimer, the term of this patent is extended or adjusted under 35 U.S.C. 154(b) by 725 days.

(21) Appl. No.: 15/107,268

(22) PCT Filed: Dec. 18, 2014

(86) PCT No.: PCT/GB2014/053758
§ 371 (c)(1),
(2) Date: Jun. 22, 2016

(87) PCT Pub. No.: WO2015/097446
PCT Pub. Date: Jul. 2, 2015

(65) Prior Publication Data
US 2017/0014184 A1 Jan. 19, 2017

(30) Foreign Application Priority Data
Dec. 23, 2013 (GB) .................................. 1322850.7

(51) Int. Cl.
*A61B 18/18* (2006.01)
*A61B 18/04* (2006.01)
(Continued)

(52) U.S. Cl.
CPC ........ *A61B 18/1815* (2013.01); *A61B 18/042* (2013.01); *A61B 18/1492* (2013.01);
(Continued)

(58) Field of Classification Search
CPC ........... A61B 2018/00589; A61B 2018/00601; A61B 2018/00607; A61B 18/042;
(Continued)

(56) References Cited

U.S. PATENT DOCUMENTS 5,207,675 A 5/1993 Canady
5,836,947 A * 11/1998 Fleischman ........ A61B 18/1492
606/47

(Continued)

FOREIGN PATENT DOCUMENTS

GB 2487199 A 7/2012
WO WO 96/27337 A1 9/1996
WO WO 2012/076844 A1 6/2012

OTHER PUBLICATIONS

International Search Report and Written Opinion issued in PCT/GB2014/053758 dated Mar. 5, 2015.
(Continued)

*Primary Examiner* — Ronald Hupczey, Jr.
*Assistant Examiner* — Bradford C. Blaise
(74) *Attorney, Agent, or Firm* — Arent Fox LLP (57) ABSTRACT

A surgical snare comprising a means of delivering thermal plasma on to biological tissue encircled by the snare. The snare may be "cold" snare, i.e. formed from insulating material, or active, i.e. connected to receive RF and/or microwave energy to be radiated into the area encircled by the snare. The surgical snare may thus deliver into biological tissue encircled by a retractable loop any one of (i) a plasma to perform surface coagulation, (ii) a non-ionising microwave field (in the absence of plasma) to perform coagulation at a deeper level, and (iii) an RF field to assist with cutting.

25 Claims, 4 Drawing Sheets (51) Int. Cl.
  *A61B 18/14* (2006.01)
  *A61B 18/00* (2006.01)
(52) U.S. Cl.
  CPC ............ *A61B 2018/0063* (2013.01); *A61B 2018/00404* (2013.01); *A61B 2018/00494* (2013.01); *A61B 2018/00589* (2013.01); *A61B 2018/00601* (2013.01); *A61B 2018/00642* (2013.01); *A61B 2018/00702* (2013.01); *A61B 2018/00744* (2013.01); *A61B 2018/00785* (2013.01); *A61B 2018/00827* (2013.01); *A61B 2018/00845* (2013.01); *A61B 2018/00869* (2013.01); *A61B 2018/00892* (2013.01); *A61B 2018/00982* (2013.01); *A61B 2018/141* (2013.01); *A61B 2018/1405* (2013.01); *A61B 2018/1407* (2013.01); *A61B 2018/1846* (2013.01); *A61B 2018/1853* (2013.01); *A61B 2018/1861* (2013.01); *A61B 2018/1892* (2013.01)
(58) Field of Classification Search
  CPC .... A61B 2018/1405; A61B 2018/1407; A61B 2018/141; A61B 18/1492; A61B 18/18; A61B 18/1815; A61B 2018/183; A61B 2018/1838; A61B 2018/1846; A61B 2018/1853; A61B 2018/1861; A61B 2018/1892; A61B 2018/00994
  See application file for complete search history.

(56) References Cited

U.S. PATENT DOCUMENTS

| | | |
|---|---|---|
| 2005/0171528 A1 | 8/2005 | Sartor et al. |
| 2007/0034211 A1* | 2/2007 | Hug .................. A61B 18/042 128/876 |
| 2008/0119843 A1 | 5/2008 | Morris |
| 2010/0036375 A1 | 2/2010 | Regadas |
| 2010/0137857 A1 | 6/2010 | Shroff et al. |
| 2012/0172864 A1 | 7/2012 | Farin et al. |
| 2012/0283732 A1* | 11/2012 | Lam ................. A61B 17/00491 606/49 |

OTHER PUBLICATIONS

British Search Report of related British Patent Application No. GB1322850.7 dated Aug. 6, 2014.

* cited by examiner

SURGICAL SNARE WITH ABILITY TO DELIVER ELECTROMAGNETIC ENERGY AND/OR THERMAL PLASMA INTO BIOLOGICAL TISSUE

CROSS-REFERENCE TO RELATED APPLICATIONS

This application is a National Stage entry of International Application No. PCT/GB2014/053758, filed Dec. 18, 2014, which claims priority to British Patent Application No. 1322850.7, filed Dec. 23, 2013. The disclosure of the prior applications are hereby incorporated in their entirety by reference.

FIELD OF THE INVENTION

The invention relates to electrosurgical apparatus in which radiofrequency and/or microwave frequency energy is used to treat biological tissue by causing haemostasis (i.e. sealing broken blood vessels by promoting blood coagulation) and, in conjunction with a flow of gas, to strike and sustain a thermal plasma. In particular, the invention relates to the use of these electrosurgical techniques in the context of a surgical snare, e.g. for use in a polypectomy procedure. For example, the invention may be applied to a surgical snare suitable for insertion down the instrument channel of an endoscope (or any other type of soaping device used in the gastrointestinal (GI) tract or elsewhere in the human or animal body), which include a means for introducing electromagnetic energy and/or thermal plasma into biological tissue.

BACKGROUND TO THE INVENTION

Argon plasma coagulation (APC) or argon beam coagulation (ABC) is a known surgical technique for controlling surface bleeding in a manner that does not require physical contact between a surgical probe delivering the plasma and the lesion. APC can be performed endoscopically, whereby a jet of argon gas is directed through a probe passed through an endoscope. Ionization of the argon gas as it is emitted creates the plasma that causes coagulation.

To strike plasma it is desirable to have a high electric field (e.g. by directly applying a high voltage or setting up a high impedance condition that causes an high voltage to exist). Typically this is done by applying a high RF voltage pulse (e.g. 500 V to 2 kV) between an active electrode and a return electrode that are separated by a small distance, e.g. less than 1 mm, for a short duration of time, e.g. in a range from 1 ms to 10 ms. The high electric field can break down the gas to initiate a plasma. In one embodiment discussed in WO 2009/060213, a high voltage (high impedance) condition is set up using a flyback circuit that uses a low frequency (e.g. radiofrequency) oscillator circuit e.g. running at 100 kHz and a transformer whose primary winding is connected to the low voltage oscillator circuit by a suitable driver and switching device (e.g. gate drive chip and a power MOSFET or BJT). The arrangement generates high voltage pulses or spikes which strike or otherwise initiate the plasma. Once struck, the impedance drops and the plasma may be maintained by a supply of microwave energy.

Polyps in the GI tract can be removed using a medical snare in an endoscopic procedure, e.g. using a colonoscope. In the case of pedunculated polyps, the snare is passed over the polyp and tightened around the polyp's neck to remove the polyp. The polyp neck may be cut by passing a radiofrequency (RF) current through the biological tissue. The current may also facilitate cauterisation.

Sessile polyps can be removed in a similar manner. It is preferable to "plump up" such polyps before removal by injecting saline or sodium hyaluronate, under the polyp to raise it away from the surrounding colon wall. This may help to reduce the risk of bowel perforation.

It is known to incorporate electrodes into the loop of a snare in order to provide an integrated means for delivering the RF current. Both monopolar, for use with a separate ground pad attached to the patient, and bipolar arrangements are known.

A disadvantage of known RF cutting snares is the high level of electrical power (in particular the use of high voltages) needed to initiate cutting action, as it carries with it the risk of unwanted thermal damage to the bowel wall. For example, the peak voltage associated with monopolar and bipolar coagulation may be in excess of 4,500 V and 450 V respectively. Moreover, the use of monopolar devices gives little or no control over the current path, which means energy may be not be accurately or controllably delivered to the desired regions of tissue.

SUMMARY OF THE INVENTION

At its most general, the present invention provides an electrosurgical device that includes a snare and a means of delivering thermal plasma on to biological tissue encircled by the snare. The snare may be a "cold" snare, i.e. formed from a piece of material (e.g. insulating material) that does not interact with the electrical components of the device. Alternatively, the snare may be active, i.e. connected to receive RF and/or microwave energy to be radiated into the area encircled by the snare. Thus, the present invention may provide an electrosurgical device that is capable of generating, within an area encircled by a surgical snare, any one of (i) a plasma to perform surface coagulation, (ii) a non-ionising microwave field (in the absence of plasma) to perform coagulation at a deeper level, and (iii) an RF field to assist with cutting.

The plasma functionality may be useful in the same way as the conventional APC technique, e.g. for treating surface bleeding, e.g. during closure of the snare. The microwave field functionality may be used to treat peptic ulcers or coagulate large blood vessels, e.g. to seal blood vessels before cutting by the snare. The RF field functionality may be used to cut through a blood vessel or region of tissue following coagulation. The RF cutting process may be performed without also requiring the application of physical force.

According to the invention, there is provided a surgical snare comprising: an elongate probe comprising a coaxial cable for conveying radiofrequency (RF) and/or microwave frequency electromagnetic (EM) energy, and a probe tip connected at the distal end of the coaxial cable for receiving the RF and/or microwave energy; a gas passage for conveying gas through the elongate probe to the probe tip; and a retractable loop mounted at the probe tip for encircling an area containing biological tissue beyond the probe tip, wherein the coaxial cable comprises an inner conductor, an outer conductor and a dielectric material separating the inner conductor from the outer conductor, wherein the probe tip comprising a first electrode connected to the inner conductor of the coaxial cable and a second electrode connected to the outer conductor of the coaxial cable, and wherein the first electrode and the second electrode are arranged to produce an electric field from the received RF and/or microwave frequency EM energy across a flow path of gas received from the gas passage to produce a thermal or non-thermal plasma in the area encircled by the retractable loop. In use, the probe tip is connected to receive radiofrequency (RF) and/or microwave frequency energy from a generator, and also defines a flow path for a gas.

In a first configuration, the probe tip defines a bipolar (e.g. coaxial) structure to produce a high electric field from the received RF and/or microwave frequency energy across the flow path for the gas to strike and sustain plasma. For example, a short pulse (e.g. having a duration of 10 ms or less, e.g. between 1 ms and 10 ms) of RF energy may be used to strike the plasma. The outlet for the plasma is at the base on the snare, and is therefore delivered into the area encircled by the snare.

The first electrode and the second electrode may be movable relative to each other into a second configuration in which the first electrode extends distally beyond the second electrode to form a radiating structure for emitting a microwave EM field outwardly from the probe tip. In the second configuration, the probe tip defines an antenna structure to emit non-ionising microwave energy into tissue. The antenna structure may be a radiating monopole antenna, which may take the form of a cylinder, a ball, a stiff wire or a helix or a turnstile antenna that is capable of emitting outwardly (i.e. away from the probe) an electric field from the received microwave frequency energy. Thus, in the first configuration the device may use one or both of RF energy and microwave energy, whereas in the second configuration, the device uses primarily microwave energy. In either configuration, the delivery of plasma or microwave energy may be interspersed with the delivery of a RF field having a waveform suitable for cutting tissue. The waveform of the RF energy used to strike the plasma may be a high amplitude pulse, whereas the waveform for cutting tissue may comprise a continuous wave having a lower amplitude.

It may be possible for the non-ionising microwave field to be generated without relative movement of the first and second electrodes, e.g. simply by delivering microwave energy in the absence of gas. However, a more uniform field effect can be produced in the area encircled by the loop if the second electrode is set back from the first electrode, i.e. the first electrode protrudes slightly into the retractable loop.

The retractable loop may be formed of insulating material, whereby it does not electrically interact with the rest of the device. However, the effectiveness of the second configuration can be enhanced if the retractable loop is made from conductive material and is coupled to the first electrode. To achieve this, the snare may include a snare base at a distal end for the coaxial cable, the snare base having a pair of feed channels, each feed channel receiving a length of the conductive material that forms the retractable loop, wherein, in the second configuration, the first electrode comprises a distal portion that protrudes into the area encircled by the retractable loop to act as a radiating microwave monopole antenna, and a proximal portion that extends through the snare base alongside the pair of feed channels. The retractable loop may thus couple energy from the proximal portion and radiate it into the area encircled by the loop.

Moreover, in this arrangement, the first electrode and the second electrode or the length of conductive material that forms the retractable loop form active and return electrodes for an RP signal conveyed by the coaxial cable. For example, the microwave monopole antenna and the retractable loop may form active and return electrodes for an RF signal conveyed by the coaxial cable. A preferential conduction path may form at the distal end of the probe when the microwave monopole antenna is in close proximity (e.g. around 0.5 mm) to either the distal end of second electrode or to a proximal portion of the retractable loop. This may enable this device to exhibit a cutting function at the distal end of the probe. This function may be particularly useful for removing a final tag of tissue held within the retractable loop.

In the first configuration, the plasma may be struck using RF or microwave energy. Microwave energy may be used to sustain the plasma after it is struck. This arrangement may offer an advantage over RF plasma used in conventional electrosurgical systems, where the electric field may collapse due to the capacitance of the cable and loading caused by tissue variations.

The impedance of the plasma is preferably matched to the impedance of the applicator (and energy delivery system) at the frequency of the microwave energy to enable efficient transfer of the microwave energy, produced by the microwave source, into the plasma. Where microwave energy is used, the applicator and/or generator may be tuned (statically or dynamically) to ensure that the plasma is matched into the load presented by the tissue. At microwave frequencies, the cable forms a distributed element transmission line, where the impedance match between applicator and energy source is determined by the source impedance of the microwave generator, the characteristic impedance of the cable (transmission line), the impedance of the applicator structure itself and the impedance of the tissue. If the characteristic impedance of the cable is the same as the output impedance of the source then all of the microwave power will be delivered into the applicator, less the attenuation caused by the cable (dielectric and conductor losses). If the impedance of the applicator and the tissue is the same as the characteristic impedance of the cable, then the maximum power available at the source will be transferred into the plasma/tissue load. Adjustments may be made to applicator structure in order to maintain the best impedance match between the applicator and the plasma/tissue load, as explained below. Adjustments may also be made at the generator or at the interface between the distal end of the first cable and the proximal end of the second (instrument) cable. These adjustments may be in the form of a change of capacitance and/or inductance of a matching network, i.e. stub tuning.

The gas may be argon, or any other suitable gas, e.g. carbon dioxide, helium, nitrogen, a mixture of air and any one of these gases, i.e. 10% air/90% helium. The high electric field for striking the plasma may be caused by creating a high impedance condition for either the RF EM energy or the microwave EM energy at the probe tip. This can be achieved through the selection of a suitable geometry for the first and second electrodes. For example, a piece of insulating dielectric material, such as quartz or other similarly low loss material, may be located between the first and second electrodes in the first configuration. This reduces the electric field inside the insulating dielectric material and causes a consequent increase in the electric field in the gas-filled gap beside the insulation dielectric material. In the first configuration, the second electrode may be arranged to extend past (e.g. more distally than) the first conductor to ensure that non-ionising radiation is not emitted.

In a preferred embodiment, the snare is capable of receiving both RF and microwave EM energy. The RF EM energy may be for striking the plasma, and may be received as a high voltage pulse. The microwave EM energy is for sustaining the plasma, i.e. delivering power into the plasma to maintain the state of ionisation. This may also be received as a pulse. The plasma may be struck repeatedly in a manner to produce a quasi-continuous beam of plasma. The advantage of this arrangement over conventional APC device which use only RF EM energy is that the plasma will not collapse due to capacitive loading or changing from a dry to wet environment. Moreover, the dual configuration nature of the instrument enables it to switch to a state suitable for deep coagulation, where the second electrode (and the insulating dielectric material) are withdrawn to a distance where the first electrode is exposed such that is acts as a radiating microwave monopole antenna structure as discussed below.

In conventional RF plasma devices, the cable capacitance and high voltages demand a high RF drive current to maintain the plasma. For example, we can apply the well known equation $$I = C \frac{dV}{dt}$$

to a quarter cycle at 400 kHz, where dt is (2.5/4) µs=625 ns. If the capacitance of the cable is 300 pF and the required peak voltage is 400 V, then I=300×400/625=0.192 A, which is relatively high. The microwave signal has a much lower voltage, e.g. around 20 V, and therefore overcomes this disadvantage.

It may also be possible to strike the plasma using the microwave frequency energy, e.g. by using a microwave resonator or an impedance transformer, i.e. a quarter wave transformer that transforms a low voltage to a higher voltage to strike plasma using a higher impedance transmission line that is a quarter wave (or an odd multiple thereof) long at the frequency of operation. This high impedance line may be switched in to strike plasma and switched out (i.e. to return to a lower impedance line) once the plasma has been struck and it is required to sustain plasma. A power PIN or varactor diode may be preferably used to switch between the two states, although it may be possible to use a co-axial or waveguide switch.

The elongate probe may comprise a sleeve surrounding the coaxial cable. The sleeve may act to protect the coaxial cable, but may also define the gas passage, e.g. as a space between an inside surface of the sleeve and an outside surface of the coaxial cable. The gas passage may have an input port located at a proximal end of the sleeve for connecting to a source of gas (e.g. a pressurised gas canister or the like).

The sleeve may further be the means for causing relative movement between the first and second electrodes. Relative movement between the first and second electrodes may be achieved by sliding a conductive (e.g. metallic) catheter over a microwave co-axial cable, whose outer conductor may also metallic. In this configuration the inner surface of the catheter (or tube that slides over the co-axial cable) must make good electrical contact with the outer conductor of the coaxial cable. This may be achieved by providing a gas permeable conductive structure that is slidable relative to the second electrode or outer electrode of the coaxial cable and permits gas to flow through it. The gas permeable conductive structure may be any one of: a conductive mesh; a cage of radially extending conductive wires or springs; and a plurality of circumferentially spaced radially protruding dents. The gas permeable conductive structure may thus provide a plurality of (e.g. four or more) circumferential connections or point contacts will need to be made to ensure that a good electrical connection is made for the microwave signal. This solution may provide a balance between having enough connection points to create an appropriate environment for the microwave energy to propagate, to allow enough gas to flow and allow the outer catheter to be moved over the co-axial cable with relative ease.

In one embodiment, the second electrode may be mounted on or formed at the distal end of the sleeve, and the sleeve may be retractable relative to the coaxial cable. In other words, the sleeve may be capable of being drawn back to reveal the first electrode at the probe tip. The sleeve may be coaxial with the coaxial cable. The first and second electrodes may thus be coaxial with each other in the first configuration. The second electrode may be an annular band of conductive material on the distal end of the sleeve. The dielectric material mentioned above may be a quartz collar mounted on the sleeve inwardly of the annular band. Alternatively or additionally, the dielectric material may be part of the inner electrode, as discussed below.

The retracting sleeve may comprise two or more telescoping sections. The telescoping sections may have a fluid tight seal therebetween to prevent the gas from escaping. The slidable outer sleeve may be retracted or extended using a mechanical or electromechanical system, i.e. a mechanical slider, a linear motor or a stepper motor arrangement. As explained below, the position of the outer sleeve with respect to the outer conductor of the co-axial cable may be determined by a return loss or impedance match/mismatch measurement made using a reflected power or forward and reflected power measurement, i.e. a reflectometer or VSWR bridge measurement, using a detector(s) within the generator or within the probe.

The first electrode may be a radiating microwave monopole antenna structure coupled to receive RF and/or microwave EM energy from the coaxial cable. The outer conductor of the coaxial cable may be grounded to form an unbalanced feed or may be floating to form a balanced feed to the antenna, i.e. where the voltage on both conductors is going up and down. Preferably the first electrode is shaped to act as a microwave antenna for emitting a microwave field corresponding to the received microwave EM radiation. For example, the monopolar radiating structure may comprise a cylinder of dielectric material having a hemispherical distal end surrounding a length of the inner conductor of the coaxial cable which protrudes beyond the outer conductor and extends through the cylinder of dielectric material to protrude at its hemispherical distal end. Other distal end shapes are possible, e.g. ball or flat end. The cylinder may be made of low loss ceramic material. The presence of the dielectric cylinder can improve the energy delivery into tissue, e.g. by reducing the amount of reflected power. The end of the length of inner conductor that protrudes from the hemispherical distal end of the cylinder may be rounded, e.g. shaped into a hemisphere, to provide a more uniform emitted field.

The probe may be used laparoscopically or may be dimensioned to be insertable through a scoping device, e.g. through the instrument channel of an endoscope, gastroscope, bronchoscope or the like. For example, the coaxial cable may have a diameter of 2.5 mm or less, preferably 2.2 mm or less. The sleeve may have an outer diameter less than 2.6 mm, preferably less than 2.5 mm. For larger laparoscopic instruments, the outer diameter may be 3 mm or more, and larger diameter co-axial cable may be used.

The retractable loop may be made from any suitable wire-like material, e.g. nitinol, nylon, metal wire or the like. Preferably the material has shape retaining properties so that it automatically adopts a loop configuration upon being released from a retracted configuration. Thus, the retractable loop may comprise a wire that extends beyond the distal end of the coaxial cable, the wire being arranged to naturally adopt a looped shape between two ends located at the distal end of the coaxial cable. The retractable loop may be adjustable to vary the length of wire between the two ends.

The retractable loop may be movable relative to the snare base, e.g. into and out of a storage channel formed in the sleeve surrounding the coaxial cable. Preferably the retractable loop is movable relative to the coaxial cable. However, it may be possible for the retractable loop to be fixed relative to the coaxial cable and for retraction to be performed by moving a tubular cover relative to the coaxial cable over the loop.

A pull wire may be connected or formed integrally with the retractable loop. The pull wire may extend to the proximal end of the coaxial cable to enable the operator to deploy the snare. The pull wire may be connected to a slider mechanism (e.g. a manual slider mechanism) at the proximal end of the device. The pull wire may be conveyed from the proximal end to the distal end through a passageway in the sleeve. It is desirable for the translation between the length of movement of the slider at the proximal end and the opening and closing of the loop (or changes in diameter once it comes out of the end of the catheter or tube) to be consistent. A thin lubricious tube may be attached (e.g. glued) to the outer jacket of the coaxial cable to act as a guide for the pull wire (or pull wires). Alternatively, a very thin walled heat-shrinkable tube could be used to attach the guide tube to the coaxial cable. The guide tube preferably runs straight along the axis of the coaxial cable.

A multi-lumen tube may be inserted inside the structure to provide separate channels or spaces for the pull wire (or pull wires) and the coaxial cable. Alternatively, a single tube may be attached to the outer conductor of the coaxial cable to contain the pull wire to prevent the pull wire from becoming twisted around the coaxial cable.

The orientation of the loop may be related to the orientation of the passageway in the sleeve. Thus, the plane of the loop may be adjustable by rotating the sleeve. Preferably the sleeve is a braided cable capable of transferring torque. A hand grip for rotating the sleeve may be mounted on, e.g. clamped to, it at the proximal end. The invention may also be expressed as an electrosurgical apparatus comprising: a radiofrequency (RF) signal generator for generating RF electromagnetic (EM) radiation having a first frequency; a microwave signal generator for generating microwave EM radiation having a second frequency that is higher than the first frequency; a surgical snare as described above connected to receive the RF EM radiation and the microwave EM radiation; a feed structure for conveying the RF EM radiation and the microwave EM radiation to the probe, the feed structure comprising an RF channel for connecting the elongate probe to the RF signal generator, and a microwave channel for connecting the elongate probe to the microwave signal generator, a gas feed connected to supply gas to the surgical snare, wherein the apparatus is operable to deliver a thermal or non-thermal plasma in the area encircled by its retractable loop.

The first electrode and the second electrode may be movable relative to each other into a second configuration in which the first electrode extends distally beyond the second electrode to form a radiating structure for emitting a microwave EM field outwardly from the probe tip, wherein the apparatus is operable to emit a non-ionising electric field outwardly from the probe tip when the first electrode and the second electrode are in the second configuration without gas supplied to thereto.

The apparatus may comprise a strike signal generation circuit arranged to cause a pulse (or pulses) of RF EM radiation to be delivered to the probe to generate the high electric field across the flow path for striking the plasma, wherein the strike signal generation circuit includes control circuitry arranged to use a detectable characteristic of a pulse of microwave EM radiation on the microwave channel to trigger generation of the pulse of RF EM radiation. The RF EM radiation is thus used to strike the plasma, whereas the microwave EM radiation is used to sustain the plasma. By coordinating the delivery of an RF strike pulse with a pulse of microwave EM radiation as described above, the apparatus is capable of striking the plasma with greater certainty.

The apparatus may further comprise a microwave signal detector for sampling forward and reflected power on the microwave channel and generating therefrom a microwave detection signal indicative of the microwave power delivered by the probe; and a controller in communication with the microwave signal detector to receive the microwave detection signal, wherein the controller is operable to select an energy delivery profile for the microwave EM radiation, the energy delivery profile for the microwave EM radiation being for coagulation of tissue, wherein the controller comprises a digital microprocessor programmed to output a microwave control signal for the microwave signal generator, the microwave control signal being for setting the energy delivery profile for the microwave EM radiation, and wherein the controller is arranged to determine a state for the microwave control signal based on the received microwave detection signal. The arrangement may be used to measure the reflected microwave signal, whereby the microwave detection signal is representative of whether or not a plasma has been struck. The signal detector may also be arranged to continuously monitor the forward and reflected microwave EM radiation to ensure that the best impedance match is maintained during plasma delivery. The microwave signal detector may comprise forward and reflected signal detectors (e.g. suitable directional power couplers on the microwave channel). The detectors may be arranged to detect signal magnitude only, e.g. they may be diode detectors. Alternatively, the detectors may be arranged to detect magnitude and phase, e.g. they may be heterodyne detectors. The microwave detection signal may thus be representative of return loss or impedance match information. The relative position of the first and second electrodes of the electrosurgical instrument may be adjustable by the controller in the surface coagulation mode (i.e. when plasma is being generated) until a set return loss threshold is reached, i.e. 8 dB, 10 dB or 12 dB.

The controller may be operable in a similar manner to select an energy delivery profile for the RF EM energy. The available profiles for the RF EM energy may include a strike pulse for generating the high electric field across the flow path for striking the plasma; and a continuous wave waveform for cutting biological tissue. The continuous wave waveform may have an amplitude one or more orders of magnitude lower than the strike pulse.

The apparatus may include a movement mechanism for causing relative movement between the first electrode and second electrode, wherein the controller is arranged to communicate a control signal to the movement mechanism based on the received microwave detection signal. The movement mechanism may be mechanical, and may be manually controlled, e.g. by the operator of the instrument. The movement mechanism may comprise an actuator, e.g.

lever or pull arm, located at the distal end of the instrument, e.g. a sliding or rotating mechanism that is moved by hand.

However, it is also contemplated herein to control the relative movement of the first and second electrode (i.e. setting the first and second configurations) in an automated manner, e.g. using an electromechanical mechanism. For example, in one embodiment, there may be a configuration controller arranged to automatically move the sleeve and operate the gas supply in accordance with the rate of blood flow at the treatment site. This feature may be used to ensure that large bleeds are dealt with in an expedient manner and that the depth of heating of healthy tissue is limited.

Furthermore, the controller may be arranged to automatically operate the movement mechanism as a means for controlling the impedance match into the plasma. Reflected and forward power measurements on the microwave channel may be used to control the position of the outer catheter with respect to the inner co-axial cable (or the inner electrode attached to the co-axial cable) by hand movement or by means of an electromechanical actuator (PZT actuator, a magnetostrictive actuator, stepper motor, linear motor) based on return loss measurements or impedance match. The occurrence of a deep or heavy bleed whilst performing ABC or surface coagulation may cause the plasma to be extinguished, which in turn would lead to the return loss measurement changing, i.e. from 10 dB (good match) to 2 dB (poor match). In the present invention, the outer sleeve may be automatically moved back to allow the microwave antenna to be deployed to enable non-ionising microwave energy to be coupled into the blood or vessel instead of ionising gas (plasma) to produce deeper coagulation to deal with the larger bleeder.

The configuration controller may include a stepper motor or linear motor connected to the sleeve or the coaxial cable to move the first and second electrodes relative to one another. The movement of the first electrode may also be based on a flow rate measurement instead of or as well as the impedance match or return loss measurement. In this instance, the mode of operation is automatically changed from surface coagulation (ABC) to deeper coagulation (extended monopole antenna to deliver non-ionising microwave radiation) to produce deep coagulation based on an increase in the rate of blood flow.

The configuration controller may be connected to a valve to control the gas supply, e.g. to switch off the supply when the instrument moves to the second configuration and to switch it on when the instrument moves to the first configuration. The valve may be part of the instrument, e.g. integrated between the sleeve and the coaxial cable, or it may be located outside the instrument, e.g. in the gas feed.

Moreover, in combination with the microwave signal detector mentioned above, the configuration controller may be arranged to control the position of the sleeve in the first configuration when the plasma is present on the basis of the microwave detection signal to minimise the reflected microwave signal. In other words, the configuration controller comprises a feedback arrangement for fine tuning the position of the sleeve in the first configuration to facilitate efficient delivery of the plasma.

While the instrument may be arranged to generate a thermal plasma when in the first configuration, it may also be arranged to generate a non-thermal plasma for sterilisation. With a co-axial applicator structure that has a plasma generating region with a diameter of between 3 mm and 5 mm, i.e. the inner diameter of the outer conductor within the co-axial structure has a diameter of between 3 mm and 5 mm, and a quartz tube that fits tightly inside with a wall thickness of between 0.25 mm and 1 mm, and where the outer diameter of the inner conductor is between 0.75 mm and 4 mm (allowing a space for gas to flow in the region between the inner conductor and the inner wall of the quartz tube), that a non-thermal plasma suitable for disinfection or sterilisation can be produced by operating the generator in pulsed mode with a duty cycle of less than 40%, e.g. 28%. In one embodiment, the rms power in a single microwave pulse is 50 W and the pulse ON time is 40 ms, within a total period of 140 ms, i.e. the average power delivered into the plasma is 14.28 W at 2.45 GHz. When an RF strike pulse is used in this configuration, the duration of the RF strike pulse is around 1 ms, and the frequency of the sinusoidal oscillations was 100 kHz. The amplitude was around 1 kV peak (707 Vrms). The RF power was less than 10% of the microwave power. The RF pulse was synchronised to the microwave burst or pulse and triggered on the rising edge of the microwave burst or pulse.

To produce thermal plasma, the duty cycle may be increased, e.g. to 50% or continuous wave (CW) and/or the rms power level may be increased, e.g. to 75 W or 100 W for this particular applicator geometry (if the geometry decreased or increased then the microwave power and the amplitude of the RF strike pulse would be adjusted accordingly). The ratio of RF to microwave power will preferably remain constant, e.g. less than 10% for non-thermal and thermal plasma.

Having the ability to perform sterilisation at the distal end of the instrument may be particularly advantageous for the purpose disinfecting the instrument channel of scopes. In order words, the non-thermal plasma is emitting as the instrument is withdrawn from the scope (e.g. endoscope or the like) to treat the inner surface of the instrument. Whilst non-thermal plasma is preferred for this process, it may also be possible to achieve sterilisation by delivering non-ionising microwave RF radiation only, i.e. in the absence of gas.

The sterilising function of the non-thermal plasma may also be used to sterilise body cavities before or after treatment. Where the device is used to clean or sterilise instruments, e.g. endoscopes or gastroscopes, the device may be configured to produce a combination of non-thermal plasma and non-ionising microwave radiation. The device may also be configured to produce non-thermal plasma, thermal plasma and non-ionising microwave radiation where it is used in NOTES procedures or where it is advantageous to be able to perform surface coagulation, sterilisation of body tissue and deep coagulation of large vessels or bleeders.

Herein, radiofrequency (RF) may mean a stable fixed frequency in the range 10 kHz to 300 MHz and microwave frequency may mean a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

BRIEF DESCRIPTION OF THE DRAWINGS

Embodiments of the invention are discussed below with reference to the accompanying drawings, in which.

DETAILED DESCRIPTION; FURTHER OPTIONS AND PREFERENCES

Figure 1:
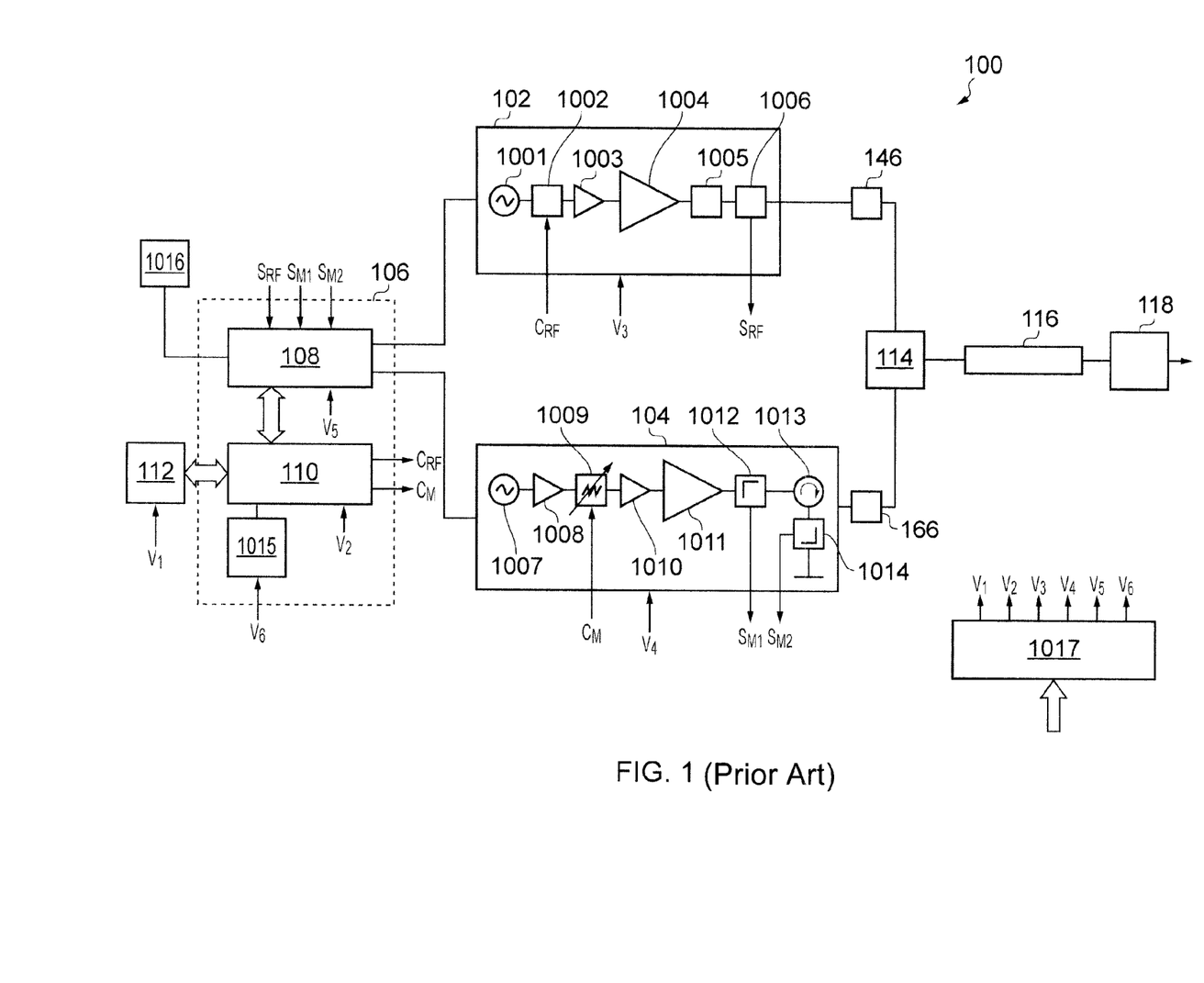
FIG. 1 is a known power delivery system suitable for use with the present invention.

FIG. 1 shows a schematic diagram of a power delivery system 100 disclosed in WO 2012/076844, which is suitable for use in the present invention.

The system 100 comprises an RF line-up 102 and a microwave line-up 104, which form parts of a RF channel and a microwave channel respectively.

The RF line-up 102 contains components for generating and controlling an RF frequency electromagnetic signal at a power level suitable for striking a plasma, as described below. In this embodiment, it includes an RF oscillator 1001, a power controller 1002, an amplifier unit (here comprising a driver amplifier 1003 and a power amplifier 1004), a transformer 1005 and an RF signal detector 1006.

The microwave line-up 104 contains components for generating and controlling a microwave frequency electromagnetic signal at a power level suitable for treating biological tissue. In this embodiment it includes a phase locked oscillator 1007, a signal amplifier 1008, an adjustable signal attenuator (e.g. an analogue or digital PIN diode based attenuator attenuator) 1009, an amplifier unit (here a driver amplifier 1010 and a power amplifier 1011), a forward power coupler 1012, a circulator 1013 and a reflected power coupler 1014. The circulator 1013 isolates the forward signal from the reflected signal to reduce the unwanted signal components present at the couplers 1012, 1014, i.e. it increases the directivity of the couplers. The circulator also protects the transistors within the high power output stage, e.g. the power GaN or GaAs transistors. It is preferable for the isolation between ports 1 to 3, 2 to 1 and 3 to 2 to be as high as possible, i.e. greater than 15 dB, or more preferably more than 20 dB.

The RF line-up 102 and microwave line-up 104 are in communication with a controller 106, which may comprise signal conditioning and general interface circuits 108, a microcontroller 110, and watchdog 1015. The watchdog 1015 may monitor a range of potential error conditions, which could result in the system not performing to its intended specification, i.e. the system delivers the wrong dosage of energy into patient tissue due to the output or the treatment time being greater than that demanded by the user. The watchdog 1015 comprises a microprocessor that is independent of the microcontroller 110 to ensure that microcontroller is functioning correctly. The watchdog 1015 may, for example, monitor the voltage levels from DC power supplies or the timing of pulses determined by the microcontroller 110. The controller 106 is arranged to communicate control signals to the components in the RF line-up 102 and microwave line-up 104. In this embodiment, the microprocessor 110 is programmed to output an RF control signal $C_{RF}$ and a microwave control signal $C_M$ for the power controller 1002 and the adjustable signal attenuator 1009 respectively. These control signals are used to set the energy delivery profile of the RF EM radiation and the microwave EM radiation output from the RF line-up 102 and microwave line-up 104 respectively. In particular, the power controller 1002 and the adjustable signal attenuator 1009 are capable of controlling the power level of the output radiation. Moreover, the power controller 1002 and the adjustable signal attenuator 1009 may include switching circuitry capable of setting the waveform (e.g. pulse width, duty cycle, and amplitude, etc.) of the output radiation.

The microprocessor 110 is programmed to output the RF control signal $C_{FR}$ and the microwave control signal $C_M$ based on signal information from the RF signal detector 1006 and forward and reflected power couplers 1012, 1014. The RF signal detector 1006 outputs a signal or signals $S_{RF}$ which are indicative of the voltage and current (and optionally the phase between the voltage and current) of the RF EM radiation on the RF channel. In this embodiment, the RF and microwave generator may be controlled by measurement of phase information only, which can be obtained from either the RF channel (from sampled current and voltage information) or the microwave channel (from sampled forward and reflected power information). The forward power coupler 1012 outputs a signal $S_{M1}$ indicative of the forward power level and the reflected power coupler 1014 outputs a signal $S_{M2}$ indicative of the reflected power level. The signals $S_{RF}$, $S_{M1}$, $S_{M2}$ from the RF signal detector 1006 and the forward and reflected power couplers 1012, 1014 are communicated to the signal conditioning and general interface circuits 108, where they are adapted to a form suitable for passing to the microprocessor 110.

A user interface 112, e.g. touch screen panel, keyboard, LED/LCD display, membrane keypad, footswitch or the like, communicates with the controller 106 to provide information about treatment to the user (e.g. surgeon) and permit various aspects of treatment (e.g. the amount of energy delivered to the patient, or the profile of energy delivery) to be manually selected or controlled, e.g. via suitable user commands. The apparatus may be operated using a conventional footswitch 1016, which is also connected to the controller 106.

The RF and microwave signals produced by the RF line-up 102 and microwave line-up 104 respectively are input to a signal combiner 114, which conveys the RF and microwave EM radiation separately or simultaneously along a cable assembly 116 to the probe 118. In this embodiment, the signal combiner 114 comprises a duplexer-diplexer unit that allows energy at microwave and RF frequencies to be transmitted along cable assembly 116 (e.g. a coaxial cable) to a probe (or applicator) 118, from which it is delivered (e.g. radiated) into the biological tissue of a patient into the instrument channel of a scope, e.g. an endoscope or another surface.

The signal combiner 114 also permits reflected energy, which returns from the probe 118 along cable assembly 116, to pass into the microwave and RF line-ups 102, 104, e.g. to be detected by the detectors contained therein. As explained below, the apparatus may include a low pass filter 146 on the RF channel and a high pass filter 166 on the microwave channel, so that only a reflected RF signal enters the RF line-up 102 and only a reflected microwave signal enters the microwave line-up 104.

Finally, the apparatus includes a power supply unit 1017 which receives power from an external source 1018 (e.g. mains power) and transforms it into DC power supply signals $V_1$-$V_6$ for the components in the apparatus. Thus, the user interface receives a power signal $V_1$, the microprocessor 110 receives a power signal $V_3$, the RF line-up 102 receives a power signal $V_3$, the microwave line-up receives a power signal $V_4$, the signal conditioning and general interface circuits 108 receives a power signal $V_5$, and the watchdog 1015 receives a power signal $V_6$.

Figure 2:
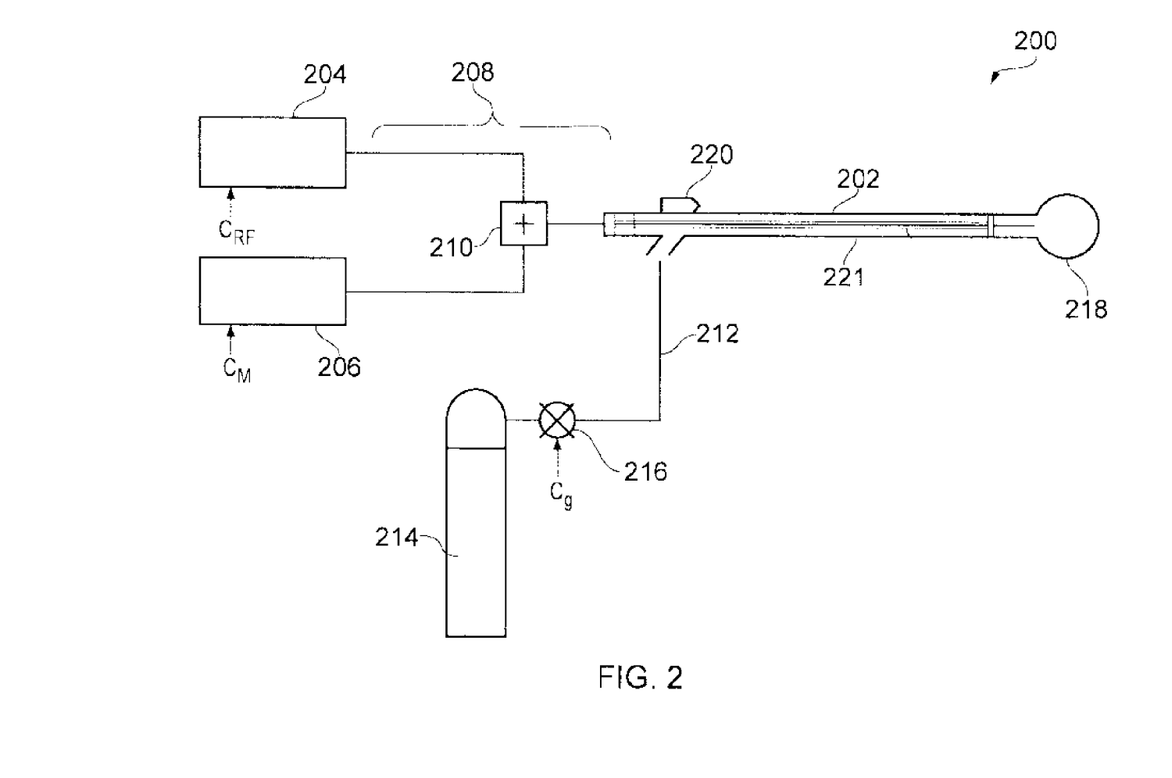
FIG. 2 is a schematic view of electrosurgical apparatus that is an embodiment of the invention.

FIG. 2 shows a schematic diagram of electrosurgical apparatus 200 that is an embodiment of the invention. The apparatus 200 comprises an electrosurgical instrument 202 capable of delivering plasma or non-ionising electromagnetic (EM) radiation from its distal end. Examples of the structure of the instrument 202 are described below.

The instrument 202 is connected to a power delivery system, which may be as described with reference to FIG. 1. However, in the embodiment of FIG. 2, the power delivery system comprises an radiofrequency (RF) radiation source 204 and a microwave radiation source 206 which are connected to deliver power to the proximal end of the instrument 202 via a feed structure 208. The feed structure 208 may include a signal combiner unit 210 as discussed above. The RF source 204 and the microwave source 206 may be arranged to output an RF signal and a microwave signal respectively based on control signals $C_{RF}$ and $C_M$ from a controller (not shown).

The instrument 202 is also connected to receive a gas, e.g. from a pressurised gas source 214 via supply line 212. A control valve 216 on the supply line 212 may be arranged to control the flow of gas received by the instrument 202, e.g. based on a control signal $C_g$ from the controller. It may be desirable to activate the gas control valve and/or flow controller prior to activating the RF and/or microwave energy sources in order to ensure that gas is present when said energy sources are activated as it is necessary for gas to be present in the plasma forming region before plasma can be generated. It may be preferable to include a gas sensor in the plasma forming region and the signals from this sensor used to control the gas flow valves. This system also helps control gas utilisation and prevents the patient from filling up with argon (or other) gas.

The RF and microwave measurement information may also be used to control the gas controller, i.e. the gas control valve may be closed when RF and/or microwave power cannot be detected using voltage/current and/or forward/reflected power monitoring circuits within the generator. It may be preferable to wait for a set period of time, i.e. 20 ms or 200 ms before shutting off the gas supply. This arrangement acts as a safety feature and as a means of controlling gas usage.

A loop of wire 218 is mounted at a distal end of the instrument 202 to form a surgical snare. The loop 218 is retractable through the operation of a slider 220 mounted on the instrument at its proximal end. The instrument 202 may comprise an outer sleeve 221 which carries a coaxial cable and gas from its proximal end to the distal end. The slider 220 is connected to the loop 218 via one or more pull wire or push rods that extend through the outer sleeve 221.

Figure 3:
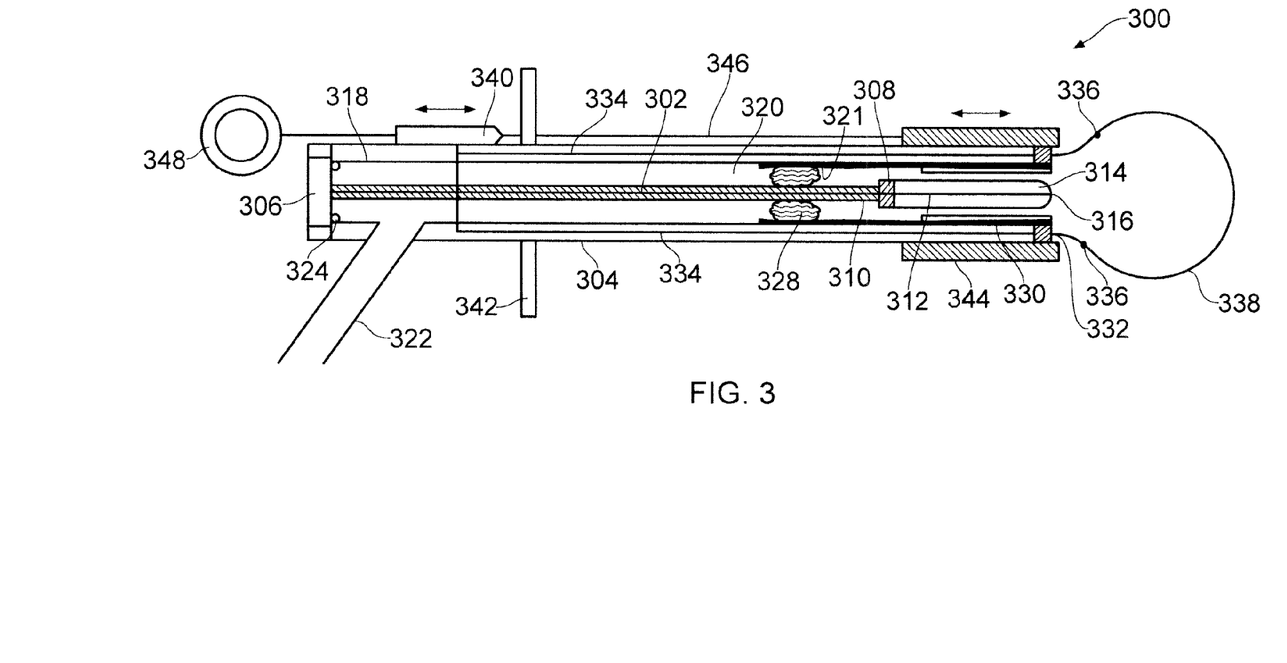
FIG. 3 is a schematic cross-sectional view of an electrosurgical device that is an embodiment of the invention.

FIG. 3 shows a first embodiment of an electrosurgical instrument 300 according to the invention. The instrument 300 comprises an elongate probe made up of a central coaxial cable 302 surrounded by a tubular sleeve 318. The proximal end of the coaxial cable 302 (shown on the left in FIG. 3) terminates at a suitable connector 306 that is adapted to connect to the feed structure that supplied the RF and microwave signals. The coaxial cable 302 conveys the RF and microwave signals to the distal end of the instrument (on the right in FIG. 3).

The distal end of the coaxial cable 302 terminates at a insulating element 308 such as a glass bead or ceramic disc positioned between the body of the coaxial cable and the cylindrical cap to prevent shorting or breakdown from occurring. Alternatively, the dielectric within the microwave cable may extended by e.g. 0.1 mm to 0.2 mm past the outer conductor of the co-axial cable. The outer conductor 310 of the coaxial cable stops at the insulating element 308, but the inner conductor 312 continues through the insulating element 308 and protrudes beyond the insulating element 308 for a length selected (using simulations) to give best impedance match for deep coagulation. The protruding length is surrounded by a cylindrical ceramic (or other suitable dielectric or magnetic material) cap 314, which terminates at its distal end in a dome 316, e.g. a hemisphere. The inner conductor 312 protrudes slightly from the dome 316. The inner conductor 312 and cylindrical cap function as a first electrode of the instrument.

The sleeve 318 surrounds the coaxial cable 302 to define an annular space 320 between the outer surface of the coaxial cable 302 and the inner surface of the sleeve 318. Radial support elements or spacers (not shown) may be used to locate the coaxial cable 302 within the sleeve. The annular space 320 may be used to transport gas to the distal end of the instrument. The base piece 318 has a port 322 in a side surface thereof that is connected to the gas supply line. A gas tight seal 324, which may be an O-ring or the like, is provided at the join between the sleeve 318 and the connector 306 in order to minimise the escape of gas. Gas introduced into the port 322 therefore flows along the annular space 320 to exit the instrument at its distal end.

The sleeve 318 has an electrically conductive inner surface 321 along a length thereof leading up to its distal end. For example, the sleeve may comprise a stainless steel shaft with a polyimide liner on its outer surface. Its electrically conductive inner surface 321 is electrically connected to the outer conductor 310 of the coaxial cable 302. In this embodiment, this is done by means of an electrically conductive mesh 328 mounted within the annular space 320. The mesh is porous, and therefore permits the gas to flow through it whilst also providing an electrical connection. This could also be achieved using a spring or a plurality of small wires electrically connected, i.e. soldered or crimped or trapped, to one or both surfaces of conductors or electrodes 310 and 321. Providing at least two, ideally at least four, circumferential contact points around the circumference of the conductor(s) can ensure good enough electrical contact for the microwave energy to propagate unimpaired. It may also be possible and preferable to put a plurality of dents or a partial crimp (e.g. around one half) in/on one of the conductors in order to make the necessary electrical contact needed whilst also enabling the gas to flow onto the plasma generating region or the distal end of the device where plasma is formed.

The electrically conductive inner surface 321 of the sleeve is further covered by an insulating tube 330 (e.g. made of quartz, ceramic or the like) along a distal length thereof that can overlap longitudinally with the cylindrical cap 314. The electrically conductive inner surface 321 and insulating tube 330 function as a second electrode of the instrument.

The sleeve 318 is contained with an outer protective sheath 304, e.g. formed of polyimide or the like. The protective sheath 304 terminates at its distal end in an annular snare base 332. The snare base 332 may be made from a suitable insulator, e.g. a low loss microwave ceramic, PTFE, PEEK, Nylon or the like.

The outer sheath 304 defines a passageway for a pair of pull wires 334 from the proximal end of the device to the distal end. Each pull wire 334 passes through the snare base 332 via a feed channel (i.e. a passageway formed in the snare base). The pair of pull wires 334 are each connected at their distal end to a respective end 336 of a length of wire 338 that forms a loop for the snare. The pair of pull wires 334 are each connected at their proximal end to a slider mechanism 340 which is movable relative to the sheath 304. The slider mechanism 340 can be operated by the user to adjust the length of wire 338 that protrudes from the sheath 304, thereby controlling the diameter of the loop formed by the length of wire 338 at the distal end of the device. The length of wire 338 may have a shape retaining property which allows it to deform in order to enter the passages in the sleeve, but recover its loop shape when drawn out again.

A handle 342 is secured to the sheath at the proximal end to enable the loop to be rotated. The sheath 342 may comprise a cable with internal metal braiding in order to efficiently transfer torque applied to the handle 342.

To avoid damaging the distal end of the device as it is inserted along the instrument channel of an endoscope, a slidable tubular cover 344 is mounted at the distal end of the sheath 304. A pull wire 346 extends from the tubular cover 344 to a handle 348 at the proximal end of the snare. The handle 348 may be operated by the user to slide the cover 344 over the retractable loop 338. In use, the cover 344 is slid back over the sheath 304 to expose the retractable loop 338.

In this embodiment, the retractable loop 338 acts as a "cold" snare, i.e. it performs no electrical function. The retractable loop 338 may be made from any suitable wire-like insulating material, e.g. nitinol, nylon or the like.

The reminder of the instrument is arranged to generate a plasma in the area encircled by the retractable loop 338 by taking the following steps:
supply gas to the distal region of the instrument (i.e. to the region between the quartz tube 330 and cylindrical cap 314),
sending a pulse of RF energy through the coaxial cable to strike a plasma in the gas at the distal region by generating a high electric field in the region, and
sending a pulse of microwave energy through the coaxial cable to sustain or maintain the plasma to ensure that appropriate treatment takes place.

The RF pulse may be automatically triggered by a characteristic (e.g. the rising edge) of the microwave pulse, so that the strike and sustain pulses are always synchronised. The RF pulse is arranged to have a voltage suitable for setting up an electric field for striking the plasma. The voltage may be between 150 V and 1500 V peak, more preferably between 250 V and 750 V peak. The frequency of the RF pulses may be between 100 kHz and 1 MHz, and may comprises a window or burst of sinusoidal waveform or signals that is time-gated (e.g. based on the detected microwave pulse), e.g. to have a duration of between 0.5 µs and 10 ms.

The delivered microwave power may be monitored (e.g. by measuring forward and reflected microwave signals) in order to check the status of the plasma.

In the embodiment above, the plasma is struck by the RF signal. In other embodiments, the plasma may be struck by the microwave signal only, because the close proximity between the inner and outer conductors enables a high electric field to be generated from the microwave signal. For example, if it is possible to deliver 25 W of CW microwave power to the distal end of the instrument then this may create a high enough electric field. One possible means of striking plasma using the microwave field is to decrease the distance between the two conductors within the plasma generating region at the time plasma is struck and then increase the distance again once it has been struck in order to create the optimal environment (impedance) for plasma to be sustained.

Figure 4A:
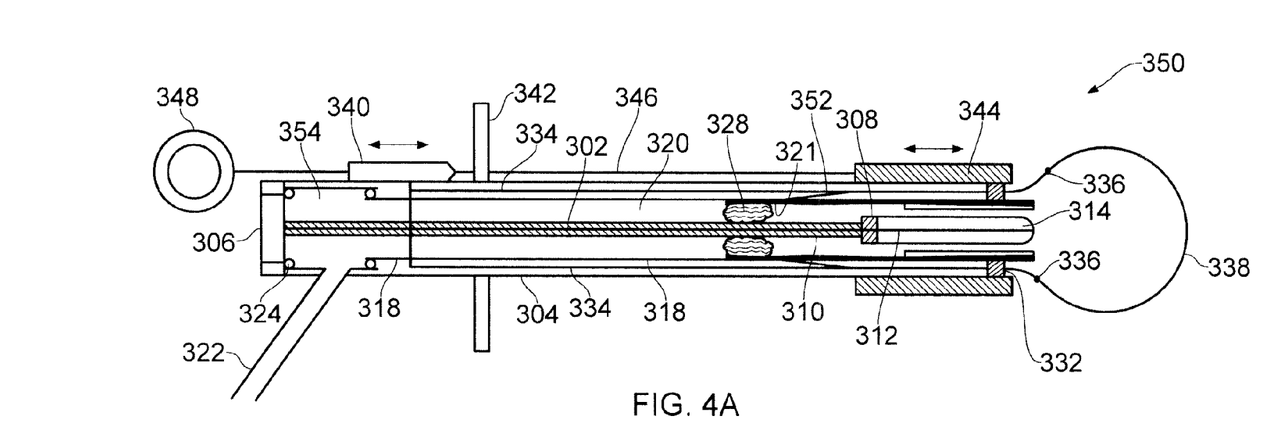
FIG. 4A is a schematic cross-sectional view of an electrosurgical instrument that is another embodiment of the invention in a first configuration.
Figure 4B:
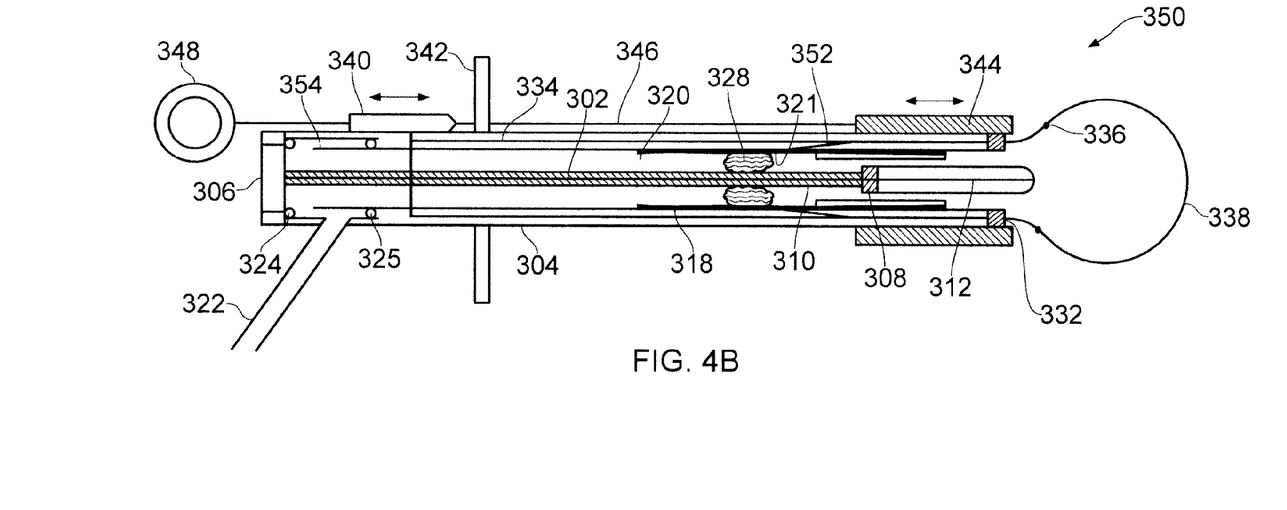
FIG. 4B is a schematic cross-sectional view of the electrosurgical instrument that of FIG. 4A in a second configuration.

FIGS. 4A and 4B are schematic cross-section views of an electrosurgical instrument 350 that is another embodiment of the invention. Components in common with FIG. 3 are given the same reference numbers and are not described again.

The embodiment in FIGS. 4A and 4B differs from the embodiment of FIG. 3 in that the surgical snare form by the retractable loop 338 is electrically active. In this embodiment, the loop 338 and at least the distal ends of the pull wires 334 are made of an electrically conductive material (e.g. metal wire).

The loop 338 is electrically connected to the outer conductor 310 of the coaxial cable 302 via an electrically conductive contact element 352. The electrically conductive contact element 352 is mounted on the outer surface of the sleeve 318 and is electrically connected to the electrically conductive inner surface 321, which is turn is connected to the outer conductor 310 of the coaxial cable 302. The contact element 352 may be a flared tube that fits over the sleeve 318. The electrically conductive inner surface 321 may include on or more tabs which protrude through the sleeve to touch the contact element 352. The flared distal end of the tube abuts the conductive part of the push wires 334 and/or loop 338.

In this embodiment, the sleeve 318 is arranged to slide in a longitudinal direction relative to the coaxial cable 302. To achieve this, the sleeve 318 is slidably mounted in a telescopic manner within a proximal base piece 354. An O-ring 325 may be fitted at the sliding interface to maintain a fluid tight seal. A pull wire (not shown) may extend through the connector 306 to assist positioning of the sleeve 318 relative to the coaxial cable. The pull wire may be manually operated, or may be connected to an automated control mechanism, e.g. a stepper motor or linear motor, which can automatically control the position of the sleeve 318, e.g. on the basis of a control signal from the controller.

The slidable sleeve permits the instrument to adopt two configurations. In a first configuration, as shown in FIG. 4A, the electrically conductive inner surface 321 of the sleeve 318 is longitudinally in line with the cylindrical cap 314. This configuration sets up a region of high impedance which exhibits a high electric field when the RF or microwave signal is supplied to the instrument. In this configuration, the instrument may be adapted to deliver plasma, e.g. thermal plasma for surface coagulation or non-thermal plasma for sterilisation, from the distal end of the probe. This mode of operation corresponds to the device shown in FIG. 3. The presence of the grounded loop does not materially affect strike of the plasma because the fields are protected within the sleeve.

The microprocessor may be arranged to output a control signal to adjust the position of the sliding sleeve relative to the coaxial cable based on the detected return loss or impedance mismatch that is determined in the controller from the microwave detection signal. This control may be done when plasma is being generated e.g. to maintain a pre-set required match or return loss, e.g. 10 dB (90% of the microwave energy is delivered into the plasma).

In a second configuration, as shown in FIG. 4B, the sleeve 318 is slid back relative to the coaxial cable 302 to expose a length of the cylindrical cap 314 at the distal end of the device. The exposed end functions as a radiating monopole microwave antenna. In this configuration, a microwave signal is supplied to the coaxial cable in the absence of gas.

The microwave signal is emitted at a non-ionising radiation field. The levels of non-ionising microwave power delivered at the distal radiating monopole may be between 2.5 W and 50 W continuous wave power; the level is dependent on the rate of blood flow or the size of the vessel being coagulated. The power level also depends on the properties of the microwave transmission cable used to deliver the microwave energy from the generator to the applicator or antenna.

Microwave energy delivered to the cylindrical cap 314 may be coupled to set up a travelling wave in the conductive parts of the pull wires 334, from where it is conveyed into and radiates from the wire loop 338. The strength of the radiated field is at a maximum at the distal end of the loop, where the travelling waves from each of the pull wires meet.

The microwave energy may be delivered as a sequence of pulses or a burst of microwave energy, whereby the mechanical force follows or is embedded within the burst of microwave coagulation energy. For example, one activation profile may comprise applying 10 W of microwave power for 10 seconds, and applying the mechanical force for shorter periods within that 10 second time frame, i.e. the mechanical and microwave energy are delivered together and microwave energy is always applied, but mechanical energy is applied at intervals within the window of application of the microwave energy.

The distal end of the cylindrical cap 314 may terminate in an electrically conductive dome, which helps to ensure that the power density in the area encircled by the snare is not too highly concentrated at the distal end of the cylindrical cap 314.

The invention claimed is:

1. A surgical snare comprising:
   an elongate probe comprising a coaxial cable for conveying radiofrequency (RF) and/or microwave frequency electromagnetic (EM) energy, and a probe tip connected at a distal end of the coaxial cable for receiving the RF and/or microwave frequency EM energy;
   a gas passage for conveying gas through the elongate probe to the probe tip; and
   a retractable loop mounted at the probe tip for encircling an area containing biological tissue beyond the probe tip,
   wherein the coaxial cable comprises an inner conductor, an outer conductor and a dielectric material separating the inner conductor from the outer conductor,
   wherein the probe tip comprises a first electrode connected to the inner conductor of the coaxial cable and a second electrode connected to the outer conductor of the coaxial cable, and
   wherein, in a first configuration, the first electrode and the second electrode are arranged to produce an electric field from the received RF and/or microwave frequency EM energy across a flow path of gas received from the gas passage to produce a thermal plasma or non-thermal plasma in the area encircled by the retractable loop.

2. A surgical snare according to claim 1, wherein the first electrode and the second electrode are movable relative to each other from the first configuration into a second configuration in which the first electrode extends distally beyond the second electrode to form a radiating structure for emitting a microwave EM field outwardly from the probe tip.

3. A surgical snare according to claim 2 including a snare base at a distal end of the coaxial cable, the snare base having a pair of feed channels, each feed channel receiving a length of a conductive material that forms the retractable loop, wherein, in the second configuration, the first electrode comprises a distal portion that protrudes into the area encircled by the retractable loop to act as a radiating microwave monopole antenna, and a proximal portion that extends through the snare base alongside the pair of feed channels.

4. A surgical snare according to claim 3, wherein the first electrode and the second electrode or the length of conductive material that forms the retractable loop form active and return electrodes for an RF signal conveyed by the coaxial cable.

5. A surgical snare according to claim 2, wherein an outer electrode of the coaxial cable is connected to the second electrode by a gas permeable conductive structure that is slidable relative to the second electrode or outer electrode of the coaxial cable and permits gas to flow through it.

6. A surgical snare according to claim 5, wherein the gas permeable conductive structure is any one of:
   a conductive mesh;
   a cage of radially extending conductive wires or springs; and
   a plurality of circumferentially spaced radially protruding dents.

7. A surgical snare according to claim 5, wherein the gas permeable conductive structure is soldered or crimped to the second electrode.

8. A surgical snare according to claim 1, wherein the elongate probe comprises a sleeve surrounding the coaxial cable, the gas passage being a space between an inside surface of the sleeve and an outside surface of the coaxial cable.

9. A surgical snare according to claim 8, wherein the second electrode is formed on a distal end of the sleeve, and the sleeve is retractable relative to the coaxial cable.

10. A surgical snare according to claim 8, wherein the sleeve comprises a rotatable braided cable to permit adjustment of an orientation of a plane of the retractable loop.

11. A surgical snare according to claim 1, wherein the first electrode is a radiating microwave monopole antenna structure coupled to receive RF and/or microwave frequency EM energy from the coaxial cable.

12. A surgical snare according to claim 11, wherein the radiating microwave monopole antenna structure comprises a cylinder of dielectric material having a hemispherical distal end surrounding a length of the inner conductor of the coaxial cable which protrudes beyond the outer conductor and extends through the cylinder of dielectric material to protrude at its hemispherical distal end.

13. A surgical snare according to claim 12, wherein an end of the length of inner conductor that protrudes from the hemispherical distal end of the cylinder is shaped into a hemisphere.

14. A surgical snare according to claim 1, wherein the elongate probe is insertable through a instrument channel of an endoscope.

15. A surgical snare according to claim 1, wherein the retractable loop comprises a wire that extends beyond a distal end of the coaxial cable, the wire being arranged to naturally adopt a looped shape between two ends located at the distal end of the coaxial cable.

16. A surgical snare according to claim 15, wherein the retractable loop is adjustable to vary a length of wire between the two ends.

17. Electrosurgical apparatus comprising:
   a radiofrequency (RF) signal generator for generating RF electromagnetic (EM) radiation having a first frequency;

a microwave signal generator for generating microwave frequency EM radiation having a second frequency that is higher than the first frequency;

a surgical snare according to claim 1 connected to receive the RF EM radiation and the microwave frequency EM radiation;

a feed structure for conveying the RF EM radiation and the microwave frequency EM radiation to the elongate probe, the feed structure comprising an RF channel for connecting the elongate probe to the RF signal generator, and a microwave channel for connecting the elongate probe to the microwave signal generator, a gas feed connected to supply gas to the surgical snare, wherein the apparatus is operable to deliver a thermal plasma or a non-thermal plasma in the area encircled by the retractable loop.

18. Electrosurgical apparatus according to claim 17, wherein the first electrode and the second electrode are movable relative to each other from the first configuration into a second configuration in which the first electrode extends distally beyond the second electrode to form a radiating structure for emitting a microwave EM field outwardly from the probe tip, and wherein the apparatus is operable to emit a non-ionising electric field outwardly from the probe tip when the first electrode and the second electrode are in the second configuration without gas supplied to thereto.

19. Electrosurgical apparatus according to claim 17 comprising a strike signal generation circuit arranged to cause a pulse of RF EM energy to be delivered to the elongate probe to generate the electric field across the flow path for striking the plasma, wherein the strike signal generation circuit includes control circuitry arranged to use a detectable characteristic of a pulse of microwave EM energy on the microwave channel to trigger generation of the pulse of RF EM energy.

20. Electrosurgical apparatus according to claim 19, wherein the controller is arranged to cause the microwave signal generator to deliver a strike pulse of microwave frequency EM energy to the elongate probe to generate the electric field across the flow path for striking the plasma.

21. Electrosurgical apparatus according to claim 17 comprising:

a microwave signal detector for sampling forward and reflected power on the microwave channel and generating therefrom a microwave detection signal indicative of microwave power delivered by the elongate probe; and a controller in communication with the microwave signal detector to receive the microwave detection signal, wherein the controller is operable to select an energy delivery profile for the microwave frequency EM energy, the energy delivery profile for the microwave frequency EM energy being for coagulation of tissue, wherein the controller comprises a digital microprocessor programmed to output a microwave control signal for the microwave signal generator, the microwave control signal being for setting the energy delivery profile for the microwave frequency EM energy, and wherein the controller is arranged to determine a state for the microwave control signal based on the received microwave detection signal.

22. Electrosurgical apparatus according to claim 21, wherein the controller is operable to select an energy delivery profile for the RF EM energy from:

a strike pulse for generating the electric field across the flow path for striking the plasma; and a continuous wave waveform for cutting biological tissue.

23. Electrosurgical apparatus according to claim 21 including a movement mechanism for causing relative movement between the first electrode and second electrode, wherein the controller is arranged to communicate a control signal to the movement mechanism based on the received microwave detection signal.

24. Electrosurgical apparatus according to claim 23, wherein the movement mechanism comprises any one of a linear motor, a stepper motor, a piezoelectric actuator, and a magnetostrictive actuator.

25. Electrosurgical apparatus according to claim 23, wherein the controller is arranged to adjustably control the movement mechanism to maintain a return loss from the elongate probe at a value of at least 10 dB.

* * * * *